United States Patent [19]
Bymaster et al.

[11] Patent Number: 6,117,890
[45] Date of Patent: Sep. 12, 2000

[54] METHOD FOR TREATING BIPOLAR DISORDER

[75] Inventors: Franklin P Bymaster, Brownsburg; Harlan E Shannon, Carmel, both of Ind.

[73] Assignee: Eli Lilly and Company, Indianapolis, Ind.

[21] Appl. No.: 09/194,710

[22] PCT Filed: Jul. 28, 1997

[86] PCT No.: PCT/US97/13185

§ 371 Date: Dec. 16, 1998

§ 102(e) Date: Dec. 16, 1998

[87] PCT Pub. No.: WO98/05324

PCT Pub. Date: Feb. 12, 1998

Related U.S. Application Data

[60] Provisional application No. 60/022,900, Aug. 1, 1996.

[51] Int. Cl.$^7$ ................ A61K 31/4436; A61K 31/4439
[52] U.S. Cl. ........................................... 514/342
[58] Field of Search ............................ 514/342

[56] References Cited

U.S. PATENT DOCUMENTS

| | | | |
|---|---|---|---|
| 5,041,455 | 8/1991 | Sauerberg et al. | 514/342 |
| 5,043,345 | 8/1991 | Sauerberg et al. | 514/342 |
| 5,328,923 | 7/1994 | Sauerberg et al. | 514/340 |
| 5,328,924 | 7/1994 | Sauerberg et al. | 514/340 |
| 5,488,056 | 1/1996 | Bodick et al. | 514/305 |
| 5,708,014 | 1/1998 | Bodick et al. | 514/342 |

FOREIGN PATENT DOCUMENTS

| | | |
|---|---|---|
| 0 307 142 A1 | 3/1989 | European Pat. Off. |
| 0 384 288 A2 | 8/1990 | European Pat. Off. |
| 0 709 094 A2 | 5/1996 | European Pat. Off. |
| 0 723 781 A2 | 7/1996 | European Pat. Off. |
| WO 94/20495 | 9/1994 | WIPO |
| WO 94/29303 | 12/1994 | WIPO |
| WO 95/05174 | 2/1995 | WIPO |
| WO 95/17185 | 6/1995 | WIPO |
| WO 96/13168 | 5/1996 | WIPO |

OTHER PUBLICATIONS

Rapaport, et al., *Biol. Psychiatry*, 29, 658–664 (1991).
Katzung, B.G., *Basic & Clinical Pharmacology*, (Appleton & Lange, Norwald), 90–94 (1995).
Sauerberg, et al., *J. Med. Chem.*, 35, 2274–2283 (1992).

*Primary Examiner*—Phyllis G. Spivack
*Attorney, Agent, or Firm*—David M. Stemerick; MaCharri Vorndran-Jones

[57] ABSTRACT

The present invention provides a method for treating or alleviating the symptoms of bipolar disorder, comprising administering an effective amount of xanomeline (3-(4-hexyloxy-1,2,5-thiadiazol-3-yl)-1,2,5,6-tetrahydro-1-methylpyridine).

8 Claims, No Drawings

METHOD FOR TREATING BIPOLAR DISORDER

This application claims benefit of provisional application Ser. No. 60/022,900 filed Aug. 1, 1996.

This invention provides a method for treating or alleviating the symptoms of bipolar disorder, comprising administering an effective amount of 3-(4-hexyloxy-1,2,5-thiadiazol-3-yl)-1,2,5,6-tetrahydro-1-methylpyridine (hereinafter referred to as "xanomeline").

Bipolar Disorder is a psychiatric condition which is prevelant across cultures and age groups. The lifetime prevalence of Bipolar Disorder can be as high as 1.6%. *DSM-IV*, p. 353 (American Psychiatric Association, Washington, D.C. 1994). Bipolar Disorder is a recurrent disorder characterized by one or more Manic Episodes immediately before or after a Major Depressive Episode or may be characterized by one or more Major Depressive Episodes accompanied by at least one Hypomanic Episode. Additionally, the symptoms must cause clinically significant distress or impairment in social, occupational, or other important areas of functioning. In some cases the Hypomanic Episodes themselves do not cause impairment; however, the impairment may result from the Major Depressive Episodes or from a chronic pattern of unpredictable mood episodes and fluctuating unreliable interpersonal and occupational functioning. The symptoms of Bipolar Disorder must not be better accounted for by a psychotic condition or due to the direct physiological effects of a medication, other somatic treatments for depression, drugs of abuse, or toxin exposure.

Bipolar Disorder is associated with a significant risk of completed suicide. Further, the patient suffering from Bipolar Disorder is likely to suffer from school truancy, school failure, occupational failure, or divorce.

Therefore, Bipolar Disorder is a serious, fairly prevelant, psychological condition which is clearly distinguished from psychotic conditions such as schizophrenia. *DSM-IV*, p. 353 (American Psychiatric Association, Washington, D.C. 1994). *DSM-IV*, p. 353 (American Psychiatric Association, Washington, D.C. 1994).

Applicants have discovered that xanomeline, thought to be a muscarinic agonist, can be useful for treating Bipolar Disorder. The present invention relates to a method of treating Bipolar Disorder. More specifically, the invention provides a method of treating Bipolar Disorder in humans using xanomeline.

As noted hereinbefore, the compound employed in the method of the present invention is known. Methods of preparing the compound, as well as pharmaceutical formulations containing the compound, are taught by Sauerberg in U.S. Pat. No. 5,043,345 (hereinafter refered to as the "'345 patent") herein incorporated by reference. The '345 patent teaches that xanomeline can be useful for treating Alzheimer's Disease and as stimulants of the cognitive function of the forebrain and hippocampus of mammals. Applicants have discovered that xanomeline can be useful for the treatment of bipolar disorder. Xanomeline may address the long felt need for treatments having an acceptable safety profile and provide effective relief to the patient suffering from bipolar disorder.

The present invention provides a method for treating bipolar disorder in humans comprising administering to a human in need thereof, an effective amount of a compound of Formula I:

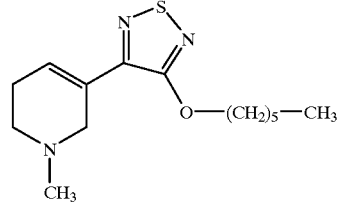

or a pharmaceutically acceptable salt or solvate thereof.

The term "effective amount", as used herein, represents an amount of compound necessary to prevent or treat a human susceptible to or suffering from Bipolar Disorder following administration to such human. The active compound is effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compound may be administered orally to humans susceptible to or suffering from Bipolar Disorder, the compound is particularly well suited to be administered transdermally. When the compound is delivered transdermally, it is preferred that the effective amount is from about 10 mg to about 100 mg per day delivery of base compound. It is especially preferred that such patch delivers an effective amount for about one to seven days.

The compound may further be delivered by a variety of other pharmaceutically accepted routes including, but in no way limited to parenterally, subcutaneous, intranasal, intramuscular and intravenous routes. Such formulations may be designed to provide delayed or controlled release using formulation techniques which are known in the art.

As used herein the term "treating" includes prophylaxis of a physical and/or mental condition or amelioration or elimination of the developed physical and/or mental condition once it has been established or alleviation of the characteristic symptoms of such condition.

As used herein, the term "Bipolar Disorder" shall refer to a condition characterized as a Bipolar Disorder, in the DSM-IV-R. *Diagnostic and Statistical Manual of Mental Disorders, Revised,* 3rd Ed. (1994) as catagory 296.xx. To further clarify, Applicants contemplate the treatment of both Bipolar Disorder I and Bipolar disorder II as described in the DSM-IV-R. The DSM-IV-R was prepared by the Task Force on Nomenclature and Statistics of the American Psychiatric Association, and provides clear descriptions of diagnostic catagories. The skilled artisan will recognize that there are alternative nomenclatures, nosologies, and classification systems for pathologic psychological conditions and that these systems evolve with medical scientific progress.

The compounds employed in the invention are not believed to act via the GABA/benzodiazepine, serotonin, or dopamine receptor systems in humans. Rather, the activity of the present compound as a treatment for Bipolar Disorder is believed to be based upon modulation of muscarinic cholinergic receptors. However, the mechanism by which the present compounds function is not necessarily the mechanism stated supra., and the present invention is not limited by any mode of operation.

Xanomeline has been studied using accepted pharmacological methods such as oxotremorine-M verses N-methylscopolamine binding studies (Freedman et al. *Br. J. Pharmacology*, 93:437–445 (1988). Xanomeline inhibited the binding of $^3$H-oxotremorine-M with an inhibition costant ($K_i$) of 2 nM. The binding of the muscarinic m1 antagonist ligand, $^3$H-pirenzepine, to m1 receptors in hippocampus and $^3$H-quinuclidinyl benzilate to m2 receptors in brain stem was inhibited with $K_i$ values of 5 and 24 nM, respectively.

Muscarinic agonists stimulate the formation of CAMP up to 10 fold in CHO m4 cells treated with pertussisi toxin and the pharmacology is consistent with the mediation by m4 receptors. Eckols K. *Soc. Neurosci Abstr.*, 21:2040 (1995). In this assay, xanomeline efficaciously and potently stimulated the formation of cAMP. Such studies suggest that xanomeline predominantly activates m1 and m4 receptors.

Xanomeline can be prepared as described in the '345 patent.

The following Examples are studies to establish the usefulness of the named compounds for treating Bipolar Disorder.

EXAMPLE 1

Human Clinical Trials

The activity of xanomeline for treating or alleviating Bipolar Disorder can be demonstrated by human clinical trials. The study was designed as a double-blind, parallel, placebo-controlled multicenter trial. The subjects were randomized into four groups, placebo and 25, 50, and 75 mg tid of test compound. The dosages were administered orally with food. Subjects were observed at four visits to provide baseline measurements. Visits 5–33 served as the treatment phase for the study.

During the visits, subjects are observed for signs of agitation, mood swings, tremor, delirium, social withdrawal, and concentration abilities.

Treatment groups are compared with respect to the number and percent of subjects who ever had the symptom during the double-blind portion of the study (visits 5 through 33), at a severity that was worse than during the baseline visits (1 through 4).

What is claimed is:

1. A method for treating Bipolar Disorder in humans comprising administering to a human in need thereof, an effective amount of a compound of Formula I:

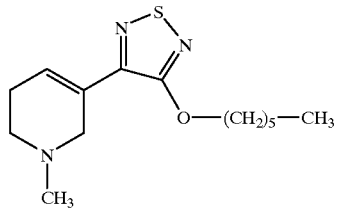

or a pharmaceutically acceptable salt thereof.

2. A method of claim 1 wherein the effective amount is from 1 mg/kg to about 100 mg/kg per day.

3. A method of claim 2 wherein the effective amount is from about 10 mg/kg to about 100 mg/kg per day.

4. A method of claim 1 wherein the effective amount is delivered using a transdermal patch.

5. A method of claim 4 wherein the transdermal patch delivers from about 10 to about 100 mg of base compound per day.

6. A method of claim 5 wherein the transdermal patch delivers an effective amount for one (1) to seven (7) days.

7. A method of claim 1 wherein the Bipolar Disorder is Bipolar Disorder I.

8. A method of claim 1 wherein the Bipolar Disorder is Bipolar Disorder II.

* * * * *